United States Patent

Geerts et al.

[11] Patent Number: 6,054,468
[45] Date of Patent: Apr. 25, 2000

[54] 1-(1H-PYRROL-2-YLMETHYL)-2-PIPERIDONE AS CELL MIGRATION INHIBITOR

[75] Inventors: Hugo Alfons Gabriel Geerts, Berchem, Belgium; Michael Joseph Kukla, Spring House, Pa.; Johan Jozef Gustave Hendrik Geysen, Retie, Belgium

[73] Assignee: Janssen Pharmaceutica, N.V., Beerse, Belgium

[21] Appl. No.: 09/194,315

[22] PCT Filed: May 26, 1997

[86] PCT No.: PCT/EP97/02775

§ 371 Date: Nov. 24, 1998

§ 102(e) Date: Nov. 24, 1998

[87] PCT Pub. No.: WO97/46552

PCT Pub. Date: Dec. 11, 1997

[30] Foreign Application Priority Data

May 31, 1996 [EP] European Pat. Off. .............. 96201501

[51] Int. Cl.$^7$ .................................................. A61K 31/445

[52] U.S. Cl. ............................................. 514/326; 546/208
[58] Field of Search ............................... 514/326; 546/208

[56] References Cited

FOREIGN PATENT DOCUMENTS

WO 96/38555   5/1996   WIPO .

OTHER PUBLICATIONS

Bogaert et al. "Vertebrate homologues of C elegans UNC–53 Protein . . . " Derwent abst. 1998—362411, 1998.
Pyrrole Mannich Bases as Potential Antipsychotic Agents, J. Med. Chem. 1992, 552–558; vol. 35. No. 3 pp. 352–358.

*Primary Examiner*—Ceila Chang
*Attorney, Agent, or Firm*—Mary A. Appollina

[57] ABSTRACT

The present invention is concerned with the compound 1-(1H-pyrrol-2-ylmethyl)-2-piperidone for use as a medicine, in particular for use as an agent for reducing excessive directional cell migration (as in metastasis); and with pharmaceutical compositions comprising a pharmaceutically acceptable carrier and the title compound as an active ingredient.

1 Claim, 1 Drawing Sheet

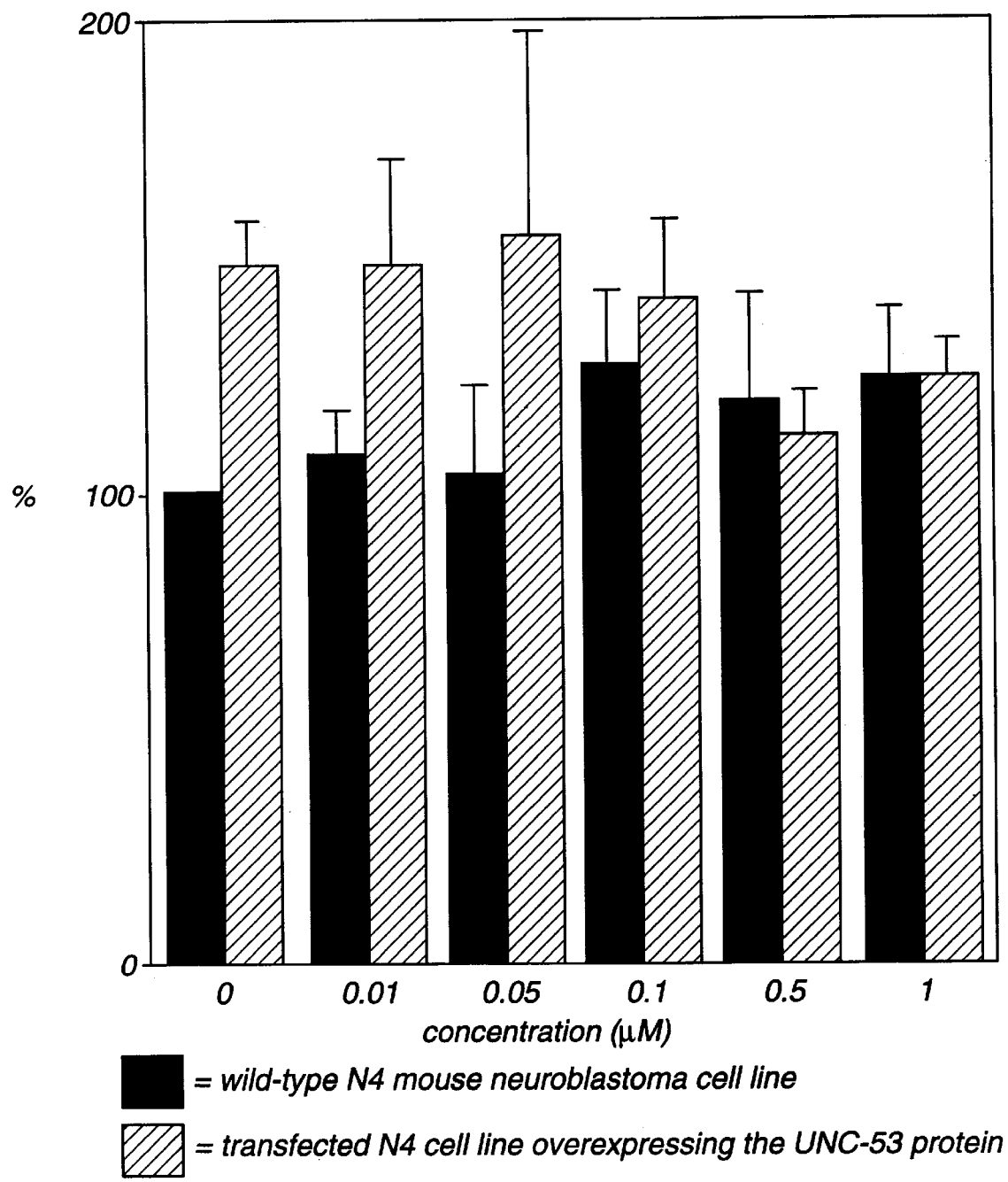

1-(1H-PYRROL-2-YLMETHYL)-2-PIPERIDONE AS CELL MIGRATION INHIBITOR

CROSS REFERENCE TO RELATED APPLICATIONS

This application is a National Stage application under 35 U.S.C. § 371 of PCT/EP97/02775 filed May 26, 1997, which claims priority from EP 96.201.501.2, filed May 31, 1996.

The present invention is concerned with the compound 1-(1H-pyrrol-2-ylmethyl)-2-piperidone for use as a medicine, in particular for use as an agent for reducing excessive directional cell migration (as in metastasis); and with pharmaceutical compositions comprising a pharmaceutically acceptable carrier and the title compound as an active ingredient.

The present invention is concerned with the compound 1-(1H-pyrrol-2-ylmethyl)-2-piperidone of formula (I)

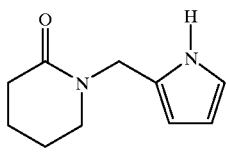

and the pharmaceutically acceptable acid addition salts thereof for use as a medicine.

The base compound 1-(1H-pyrrol-2-ylmethyl)-2-piperidone is known from *J. Med. Chem.*, 1992, 35 (3), 552–8 for use as an intermediate in the manufacture of antipsychotic agents. Hitherto, the compound was not known to have pharmacological activity.

Pharmaceutically acceptable acid addition salts are novel and comprise the therapeutically active, non-toxic salt forms obtained by treating a base form with an acid such as, for example, an inorganic acid, e.g. hydrochloric, hydrobromic, sulfuric, nitric, phosphoric acid ; or an organic acid, e.g. acetic, propanoic, hydroxyacetic, lactic, pyruvic, malonic, succinic, maleic, fumaric, tartaric, citric, methanesulfonic, ethanesulfonic, benzenesulfonic, p-toluenesulfonic, cyclamic, salicylic, p-aminosalicylic, pamoic acid. The compound of formula (I) is preferably in the base form for use as a medicine.

The compound 1-(1H-pyrrol-2-ylmethyl)-2-piperidone can conveniently be prepared by condensing 1H-pyrrol-2-carboxaldehyde with methyl 5-aminopentanoate to the corresponding imine, and then reducing the imine to the secondary amine which will cyclize to the title compound. The first condensation step can be performed in any aprotic solvent, in the presence of a dehydrating agent, optionally in the presence of an acid or base. Suitable aprotic solvents are, for example, halogenated hydrocarbons such as di- and trichloromethane. Suitable dehydrating agents are, for example, 50 nm molecular sieves, anhydrous salts such as anhydrous copper sulphate. Acid and base catalysts which can be used are, for example, p-toluenesulfonic acid and triethylamine.

The reduction-cyclization step can be performed by catalytically hydrogenating the imine compound at room temperature in an appropriate solvent. Suitable catalysts are platinum oxide, platinum-on-charcoal and palladium-on-charcoal. Appropriate solvents are alcohols, in particular ethanol, esters, e.g. ethyl acetate, ethers, e.g. tetrahydrofuran.

In UK Patent Application No. 9510944.3 filed Jun. 1, 1995 and in PCT/EP96/02311 (published as WO-96/38555 on Dec. 12, 1996) which claims priority of said UK Patent Application and which was filed concommittantly with the priority application of the instant patent application, there are described processes for the identification of compounds which inhibit or enhance the direction of cell migration, and the use of such compounds in the regulation of directional cell migration. The patent applications referred to elucidate the key role of the UNC-53 protein in the control of directional cell migration. Increased UNC-53 protein activity was found to be proportional to increased growth cone extension in the correct direction of cell migration. Inhibitors and enhancers of the unc-53 gene or the UNC-53 protein were predicted to affect the cell motility; inhibitors thus have utility in—amongst other disorders and diseases—oncology, in particular in metastasis.

Unexpectedly, the compound 1-(1H-pyrrol-2-ylmethyl)-2-piperidone has now been identified as an inhibitor of directional cell migration in assays as disclosed in the patent applications referred to above. One such assay is described in more detail in the experimental part hereunder, and the results of said assay are in addition summarized in FIG. 1. In FIG. 1, the black blocks refer to a wild-type N4 mouse neuroblastoma cell line and the hatched blocks to a transfected N4 cell line overexpressing the UNC-53 protein (cell-line deposited under LMBP Accession No. 1549CB at the Belgian Coordinated Collections of Micro-organisms (BCCM) at the Laboratorium voor Moleculaire Biologie—Plasmidencollectie—B-9000 Ghent, Belgium, in accordance with the provisions of the Budapest Treaty of Apr. 8, 1977).

In view of the experimental results described hereinafter, the present invention particularly concerns the compound 1-(1H-pyrrol-2-ylmethyl)-2-piperidone for use as a metastasis inhibitor.

Alternatively, the present invention concerns the use of the compound 1-(1H-pyrrol-2-ylmethyl)-2-piperidone for the manufacture of a medicament for the treatment of disorders or diseases wherein directional cell migration is excessive, more in particular wherein said disorder or disease is metastasis.

The present invention also is concerned with a method of treating warm-blooded animals suffering from disorders or diseases wherein directional cell migration is excessive, more in particular wherein said disorder or disease is metastasis, said method comprising administering to said animal a therapeutically effective amount of the compound 1-( 1H-pyrrol-2-ylmethyl)-2-piperidone.

The present invention also is concerned with a pharmaceutical composition comprising a pharmaceutically acceptable carrier and as an active ingredient an effective amount of the compound 1-(1H-pyrrol-2-ylmethyl)-2-piperidone, or a pharmaceutically acceptable acid addition salt form thereof. Further, the invention involves a process of preparing such a pharmaceutical composition, characterized in that the active ingredient is intimately mixed with the pharmaceutically acceptable carrier.

Pharmaceutical compositions of the compound of formula (I) suitable as medicaments according to the present invention comprise one or more excipients or carriers as known in the art. By appropriately selecting one or more of these excipients or carriers, the pharmaceutical compositions are adapted for oral, rectal, vaginal, topical, parenteral (including intramuscular, subcutaneous and intravenous) or implant administration or in a form suitable for administration by inhalation or insufflation. The formulations may, where appropriate, be conveniently presented in discrete dosage units.

Processes of preparing such compositions are well known in the art and are characterized in that the active ingredient and the excipient are intimately mixed with one another. All processes include the step of bringing into association the active compound with liquid carriers or finely divided solid carriers or both and then, if necessary, shaping the product into the desired formulation.

For oral administration, the pharmaceutical compositions may take the form of solid dose forms, for example, tablets or capsules prepared by conventional means with pharmaceutically acceptable excipients such as binding agents (e.g. pregelatinised starch, polvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For topical administration in the mouth, the pharmaceutical compositions may take the form of buccal or sublingual tablets, drops or lozenges formulated in conventional manner.

For topical administration to the epidermis the compounds of the invention may be formulated as creams, gels, ointments or lotions or as transdermal patches. Such compositions may, for example, be formulated with an aqueous or oily base with the addition of suitable thickening, gelling, emulsifying, stabilising, dispersing, suspending, and/or colouring agents.

The compound of formula (I) may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compound of formula (I) may be formulated for parenteral administration by injection, conveniently intravenous, intramuscular or subcutaneous injection, for example by bolus injection or continuous intravenous infusion. Formulations for injection may be presented in unit dosage form e.g. in ampoules, or in multidose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water.

The compound of formula (I) may also be formulated in rectal compositions such as suppositories or retention enemas, e.g. containing conventional suppository bases such as cocoa butter or other glycerides.

For intranasal administration the compound of formula (I) may be used, for example, as a liquid spray, as a powder or in the form of drops.

For administration by inhalation the compound of formula (I) are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, 1,1,1,2-tetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch. Any of the pharmaceutical compositions described above may be presented in a conventional manner associated with controlled release forms.

Preferably, the pharmaceutical compositions according to the invention are suitable for oral administration.

The compositions may advantageously be presented in discrete dose units, especially in unit dosage forms. A convenient unit dose formulation contains the active ingredient in an amount of from 0.1 to 100 mg. The amount of a compound of formula (I) required as daily dose in treatment will vary not only with the particular compound selected, but also with the route of administration, the nature of the condition being treated and the age, weight and condition of the patient and will ultimately be at the discretion of the attendant physician. In general, however, a suitable dose will be in the range of from about 0.5 to about 20 mg per day.

The desired dose may conveniently be presented in a single dose or as divided doses administered at appropriate intervals, for example as two, three, four or more sub-doses per day. Upon reiterated or chronic administration, plasma levels will progressively increase until a steady state is reached.

The compound of formula (I) may also be used in combination with other agents used in the treatment of disorders and diseases wherein directional cell migration is excessive (as in metastasis). The combination may be administered separately, i.e. simultaneously, concurrently or consecutively by any of the routes described above, or the combination may also be presented in the form of one pharmaceutical formulation. Thus, a pharmaceutical product comprising (a) a compound of formula (I) and (b) another therapeutic agent as defined hereinbefore, as a combined preparation for simultaneous, separate or sequential use in the therapeutic or prophylactic treatment of animals suffering from disorders or diseases wherein directional cell migration is excessive, comprises a further aspect of the invention. Such a product may comprise a kit comprising a container containing a pharmaceutical composition of a compound of formula (I), and another container comprising a a pharmaceutical composition of the second therapeutic agent. The product with separate compositions of the two active ingredients has the advantage that appropriate amounts of each component, and timing and sequence of administration can be selected in function of the patient.

When a compound of formula (I) is used in combination with a second therapeutic agent, the dose of each compound may vary from that when the compound is used alone. Thus when a compound of formula (I) is used together with a second therapeutic agent the dose of each compound may be the same or more commonly, lower, than that employed when the compound is used alone. Appropriate doses will be readily appreciated by those skilled in the art.

Experimental Part

EXAMPLE 1
Preparation of 5-[[(1H-pyrrol-2-yl)methylen]amino]pentanoate

To a stirred solution of 150 g of 1H-pyrrol-2-carboxaldehyde in 1500 g of trichloromethane were added 690 g of 50 nm molecular sieves. A hot solution of 264 g of methyl 5-aminopentanoate hydrochloride in 1500 g of trichloromethane was added. After stirring for 5 minutes, 465 g of triethylamine was added over ten minutes. The reaction mixture was stirred for 20 hours at ambient temperature. The reaction mixture was filtered over diatomaceous earth and the filtrate was concentrated by evaporation of the solvent. The concentrate was triturated in 1,1'-oxybisethane. The precipitate was filtered off and the filtrate was concentrated, yielding 300 g (91.1%) of 5-[[(1H-pyrrol-2-yl)methylen]amino]pentanoate.

EXAMPLE 2
Preparation of 1-(1H-pyrrol-2-ylmethyl)-2-piperidone.

A mixture of 150 g of 5-[[(1H-pyrrol-2-yl)methylen]amino]pentanoate and 120 g of ethanol was hydrogenated at $3.10^5$ Pa and at ambient temperature with 3.3 g of platinum oxide. After the calculated amount of hydrogen was consumed, the catalyst was filtered off and the filtrate was evaporated. The residue was dissolved in dichloromethane and the organic phase was washed three times with a sodium hydroxide 3N solution. The product was distilled at 13.30 Pa (bp. 100–130° C. The residue was crystallized from cyclohexane and hexane. The product was filtered off and dried, yielding 193 g (100%) of 1-(1H-pyrrol-2-ylmethyl)-2-piperidone; mp. 105.8° C.

EXAMPLE 3
Effect of 1-(1H-pyrrol-2-ylmethyl)-2-piperidone.

The effect of 1-(1H-pyrrol-2-ylmethyl)-2-piperidone on the morphological differentiation in wild-type N4 mouse neuroblastoma cells (Dr. Joniau, KU Leuven, Belgium), and N4 mouse neuroblastoma cells transfected with unc-53 (cell-line deposited under LMBP Accession No. 1549CB) was assessed as follows.

Both cell types were routinely grown for 24 hours at 37° C. in DMEM supplemented with 10% Foetal Calf Serum. All cultures were maintained in a humified atmosphere of 95/5% air CO2. After mechanical dislodging, the cells were plated on sterilized coverslips containing N2 components (Bottenstein & Sato, Proc. Natl. Acad. Sci. USA 76,514–517,1979).

Cultures of both cell types were then subjected for 24 hours to increasing concentrations of 1-(1H-pyrrol-2-ylmethyl)-2-piperidone (0, 0.01, 0.05, 0.1, 0.5 and 1 μM). Morphological changes of neurones were quantitated as described in Geerts et al., Res. Neurology & Neuroscience, 4, 21–32, 1992). Briefly, at appropriate times, glutaraldehyde was applied to the cell cultures. No washing steps were performed. This ensured that the morphology of the cells at that time point was frozen. The cells were observed in transmitted light mode on an Axiovert microscope, equipped with a Marzhauser scanning stage driven by a Indy workstation (Silicon Graphics). Images were captured using a MC5 video camera (HCS). About 3000 cells were detected in 64 neatly aligned images, forming a 8×8 square matrix of images. The exact alignment of the images ensured that neurites could be followed from one image field into the next. The analysis software automatically detected cell bodies and neurites and saved cell body size and length of each individual neurite on a file. Different parameters were subsequently calculated. The neurite length per cell was calculated on freely lying cells (not within a cluster). The fraction positive cells was defined as the fraction of cells having at least one neurite with a length exceeding twice the cell body diameter. The results of the experiment are summarized in FIG. 1.

FIG. 1 shows that in the absence of 1-(1H-pyrrol-2-ylmethyl)-2-piperidone, the fraction of positive cells is significantly higher in the transfected N4 mouse neuroblastoma cells, compared to the wild-type N4 mouse neuroblastoma cells. Thus, the transfected cells overexpress UNC-53 protein. At increasing concentrations of the compound (I), there is no (or at most a small stimulatory) effect on the wild-type N4 mouse neuroblastoma cells. On the transfected N4 mouse neuroblastoma cells, however, the compound dose-dependently attenuates the increased morphological phenotype. The results indicate that the compound 1-(1H-pyrrol-2-ylmethyl)-2-piperidone counteracts the effects of overexpression of UNC-53, and may have beneficial effects in disorders and diseases wherein directional cell migration is excessive, e.g., in metastasis. At concentrations exceeding 1 μM, the compound becomes toxic for both types of cells under the experimental conditions.

What is claimed is:

1. A method of treating a warm-blooded animal suffering from metastasis comprising administering a therapeutically effective amount of the compound 1-(1H-pyrrol-2-ylmethyl)-2-piperidone of formula (I)

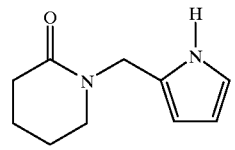

(I)

or a pharmaceutically acceptable acid addition salt thereof.

* * * * *